United States Patent
Kim et al.

(10) Patent No.: US 7,153,325 B2
(45) Date of Patent: Dec. 26, 2006

(54) PROSTHETIC INTERVERTEBRAL DISC AND METHODS FOR USING THE SAME

(75) Inventors: Daniel H. Kim, Mountain View, CA (US); Kunwoo Lee, Mountain View, CA (US); Curtis W. Frank, Mountain View, CA (US); Sung Kyu Ha, Mountain View, CA (US)

(73) Assignee: Ultra-Kinetics, Inc., Mountain View, CA (US)

( * ) Notice: Subject to any disclaimer, the term of this patent is extended or adjusted under 35 U.S.C. 154(b) by 0 days.

(21) Appl. No.: 10/632,538

(22) Filed: Aug. 1, 2003

(65) Prior Publication Data

US 2005/0027364 A1    Feb. 3, 2005

(51) Int. Cl.
A61F 2/44 (2006.01)
A61B 17/56 (2006.01)
(52) U.S. Cl. .................. 623/17.15; 623/17.16
(58) Field of Classification Search ... 623/17.11–17.16
See application file for complete search history.

(56) References Cited

U.S. PATENT DOCUMENTS

| | | | |
|---|---|---|---|
| 3,867,728 A | 2/1975 | Stubstad et al. |
| 5,002,576 A | 3/1991 | Fuhrmann et al. |
| 5,039,519 A | 8/1991 | Inoue et al. |
| 5,171,281 A | 12/1992 | Parsons et al. |
| 5,221,431 A | 6/1993 | Choe et al. |
| 5,221,432 A | 6/1993 | Choe et al. |
| 5,314,477 A | 5/1994 | Marnay |
| 5,370,697 A | 12/1994 | Baumgartner |
| 5,458,642 A | 10/1995 | Beer et al. |
| 5,545,229 A | 8/1996 | Parsons et al. |
| 6,156,067 A | 12/2000 | Bryan et al. |
| 6,166,067 A | 12/2000 | Kramer et al. |
| 6,258,125 B1 | 7/2001 | Paul et al. |
| 6,264,695 B1 | 7/2001 | Stoy |
| 6,436,137 B1 | 8/2002 | Wang et al. |
| 6,527,804 B1 | 3/2003 | Gauchet et al. |
| 6,533,818 B1 | 3/2003 | Weber et al. |
| 6,582,466 B1 | 6/2003 | Gauchet |
| 6,582,468 B1 | 6/2003 | Gauchet |
| 6,626,943 B1 | 9/2003 | Eberlein et al. |
| 6,682,562 B1 | 1/2004 | Viart et al. |
| 6,692,495 B1 | 2/2004 | Zacouto |
| 6,726,721 B1 | 4/2004 | Stoy et al. |
| 6,733,533 B1 | 5/2004 | Lozier |
| 6,746,485 B1 | 6/2004 | Zucherman et al. |

(Continued)

OTHER PUBLICATIONS

Takahata et al. "Bone Ingrowth Fixation of Artificial Intervertebral Disc Consisting of Bioceramic-Coated Three-dimensional Fabric" Spine, vol. 28, No. 7, pp. 637-644.

(Continued)

*Primary Examiner*—Thomas Barrett
(74) *Attorney, Agent, or Firm*—Orrick, Herrington & Sutcliffe LLP

(57) ABSTRACT

A prosthetic intervertebral disc and methods for using the same are provided. The subject prosthetic discs are characterized by including top and bottom endplates separated by a fibrous compressible element that includes an annular region and a nuclear region. The two plates are held together at least one fiber wound around at least one region of the top endplate and at least one region of the bottom endplate. The subject discs may be employed with separate vertebral body fixation elements, or they may include integrated vertebral body fixation elements. Also provided are kits and systems that include the subject prosthetic discs.

16 Claims, 8 Drawing Sheets

U.S. PATENT DOCUMENTS 6,749,635 B1 6/2004 Bryan
6,827,740 B1 12/2004 Michelson
2003/0045939 A1 3/2003 Casutt
2003/0135277 A1 7/2003 Bryan et al.

OTHER PUBLICATIONS

Hudgins, Robert Garryl, "Development and Characterization of a Prosthetic Intervertebral Disc" A Thesis Presented to the Academic Faculty, Georgia Institute of Technology (Nov. 1998, pp. 1-209).

*FIG. 8*
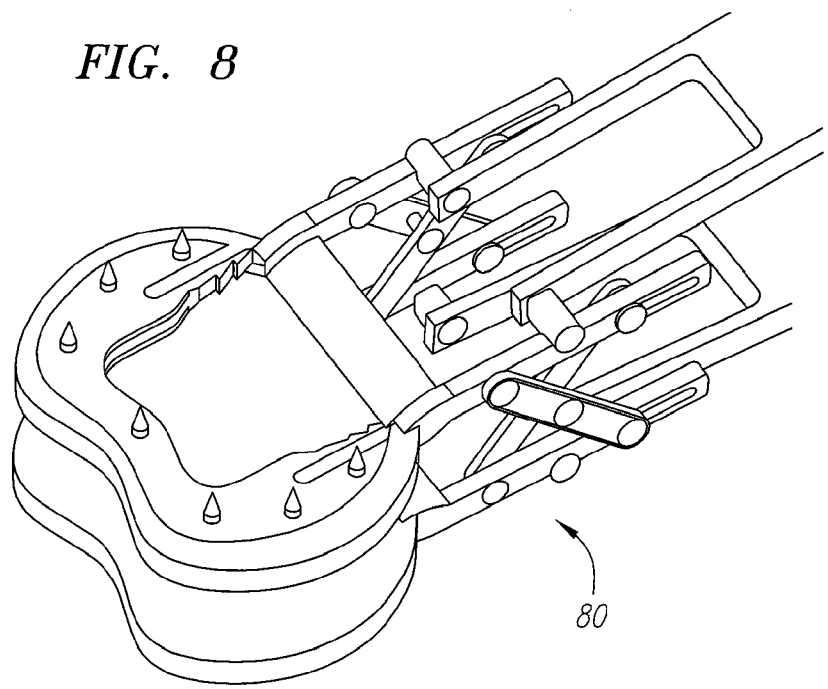
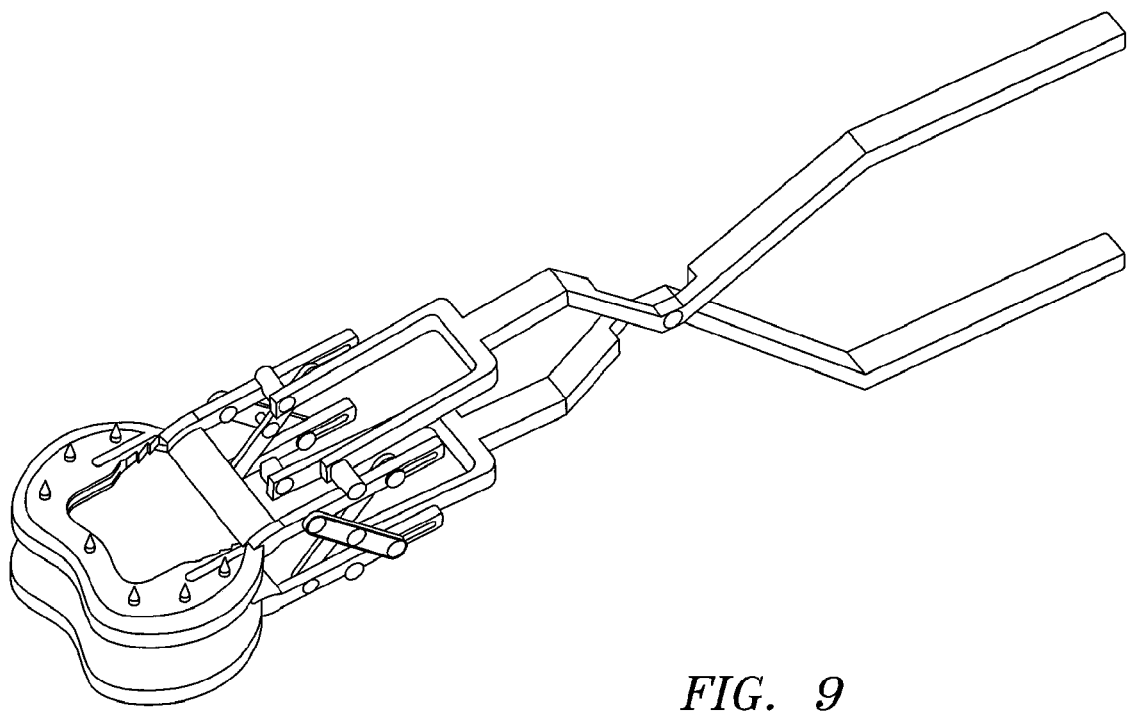
*FIG. 9*

PROSTHETIC INTERVERTEBRAL DISC AND METHODS FOR USING THE SAME

BACKGROUND OF THE INVENTION

The intervertebral disc is an anatomically and functionally complex joint. The intervertebral disc is composed of three component structures: (1) the nucleus pulposus; (2) the annulus fibrosus; and (3) the vertebral endplates. The biomedical composition and anatomical arrangements within these component structures are related to the biomechanical function of the disc.

The spinal disc may be displaced or damaged due to trauma or a disease process. If displacement or damage occurs, the nucleus pulposus may herniate and protrude into the vertebral canal or intervertebral foramen. Such deformation is known as herniated or slipped disc. A herniated or slipped disc may press upon the spinal nerve that exits the vertebral canal through the partially obstructed foramen, causing pain or paralysis in the area of its distribution.

To alleviate this condition, it may be necessary to remove the involved disc surgically and fuse the two adjacent vertebra. In this procedure, a cage is inserted in the place originally occupied by the disc and it is secured between the neighboring vertebra by the screws and plates/rods attached to the vertebra. Despite the excellent short-term results of such a "spinal fusion" for traumatic and degenerative spinal disorders, long-term studies have shown that alteration of the biomechanical environment leads to degenerative changes at adjacent mobile segments. The adjacent discs have increased motion and stress due to the increased stiffness of the fused segment. In the long term, this change in the mechanics of the motion of the spine causes these adjacent discs to degenerate.

To circumvent this problem, an artificial intervertebral disc replacement has been proposed as an alternative approach to spinal fusion. Although various types of artificial intervertebral discs have been developed to restore the normal kinematics and load-sharing properties of the natural intervertebral disc, they can be grouped into two categories, i.e., ball and socket joint type discs and elastic rubber type discs.

Artificial discs of ball and socket type are usually composed of metal plates, one to be attached to the upper vertebra and the other to be attached to the lower vertebra, and a polyethylene core working as a ball. The metal plates have concave areas to house the polyethylene core. The ball and socket type allows free rotation between the vertebra between which the disc is installed and thus has no load sharing capability against the bending. Artificial discs of this type have a very high stiffness in the vertical direction, they cannot replicate the normal compressive stiffness of the natural disc. Also, the lack of load bearing capability in these types of discs causes adjacent discs to take up the extra loads resulting in the eventual degeneration of the adjacent discs.

In elastic rubber type artificial discs, an elastomeric polymer is embedded between metal plates and these metal plates are fixed to the upper and the lower vertebrae. The elastomeric polymer is bonded to the metal plates by having the interface surface of the metal plates be rough and porous. This type of disc can absorb a shock in the vertical direction and has a load bearing capability. However, this structure has a problem in the interface between the elastomeric polymer and the metal plates. Even though the interface surfaces of the metal plates are treated for better bonding, polymeric debris may nonetheless be generated after long term usage. Furthermore, the elastomer tends to rupture after a long usage because of its insufficient shear-fatigue strength.

Because of the above described disadvantages associated with either the ball/socket or elastic rubber type discs, there is a continued need for the development of new prosthetic disc devices.

Relevant Literature

U.S. Pat. Nos. 3,867,728; 5,039,549; 5,171,281; 5,221,431; 5,221,432; 5,370,697; 5,545,229; 6,264,695; 6,533,818; 6,582,466; 6,582,468. Also of interest are published U.S. Application Nos. 20030045939 and 20030045940. See also Masahikio Takahata, Yasuo Shikinami, Akio Minami, "Bone Ingrowth Fixation of Artificial Intervertebral Disc Consisting of Boioceramic-Coated Three-dimensional Fabric," SPINE, Vol 28, No 7, pp 637–644, 2003.

SUMMARY OF THE INVENTION

A prosthetic intervertebral disc and methods for using the same are provided. The subject prosthetic discs are characterized by including top and bottom endplates separated by a fibrous compressible element that includes an annular region and a nuclear region. The two plates are held together by at least one fiber wound around at least one region of the top endplate and at least one region of the bottom endplate. The subject discs may be employed with separate vertebral body fixation elements, or they may include integrated vertebral body fixation elements. Also provided are kits and systems that include the subject prosthetic discs.

BRIEF DESCRIPTION OF THE FIGURES

FIG. 3C illustrates the manner in which the 2D fabrics in FIG. 3B are stitched together.

FIG. 4A provides a three-dimensional top view of a prosthetic disc according to an embodiment of the present invention in which the fixation elements are integral to the disc, while

FIGS. 8 and 9 provide views of vertebral body fixation elements being held in an implantation device according to an embodiment of the subject invention.

DESCRIPTION OF THE SPECIFIC EMBODIMENTS

Figure 1A:
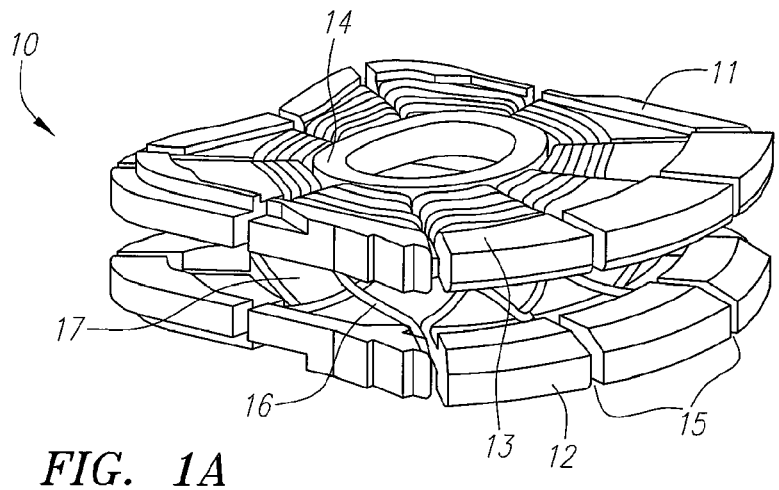
FIGS. 1A and 1B provide a three dimensional view of two different prosthetic discs according to the subject invention.

A prosthetic intervertebral disc and methods for using the same are provided. The subject prosthetic discs are characterized by including top and bottom endplates separated by a fibrous compressible element that includes an annular region and a nuclear region. The two plates are held together by at least one fiber wound around at least one region of the top endplate and at least one region of the bottom endplate. The subject discs may be employed with separate vertebral body fixation elements, or they may include integrated vertebral body fixation elements. Also provided are kits and systems that include the subject prosthetic discs.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The figures shown herein are not necessarily drawn to scale, with some components and features being exaggerated for clarity.

In further describing the subject invention, the subject prosthetic intervertebral discs will be described first in greater detail, followed by a review of representative methods for using the subject prosthetic discs, as well as a review of systems and kits that include the subject prosthetic discs.

Prosthetic Intervertebral Disc

As summarized above, the subject invention is directed to a prosthetic intervertebral disc. By prosthetic intervertebral disc is meant an artificial or manmade device that is configured or shaped so that it can be employed as a replacement for an intervertebral disc in the spine of a vertebrate organism, e.g., a mammal, such as a human. The subject prosthetic intervertebral disc has dimensions that permit it to substantially occupy the space between two adjacent vertebral bodies that is present when the naturally occurring disc between the two adjacent bodies is removed, i.e., a void disc space. By substantially occupy is meant that it occupies at least about 75% by volume, such as at least about 80% by volume or more. The subject discs may have a roughly bean shaped structure analogous to naturally occurring intervertebral body discs which they are designed to replace. In many embodiments the length of the disc ranges from about 15 mm to about 50 mm, such as from about 18 mm to about 46 mm, the width of the disc ranges from about 12 mm to about 30 mm, such as from about 14 mm to about 25 mm and the height of the disc ranges from about 3 mm to about 13 mm, such as from about 5 mm to about 12 mm.

The subject discs are characterized in that they include both an upper (or top) and lower (or bottom) endplate, where the upper and lower endplates are separated from each other by a fibrous compressible element, where the combination structure of the endplates and fibrous compressible element provides a prosthetic disc that functionally closely mimics real disc. A feature of the subject prosthetic discs is that the top and bottom endplates are held together by at least one fiber, e.g., of the fibrous compressible element, wound around at least one portion of each of the top and bottom endplates. As such, the two endplates (or planar substrates) are held to each other by one or more fibers that are wrapped around at least one domain/portion/area of the upper endplate and lower endplate such that the plates are joined to each other.

Figure 1B:
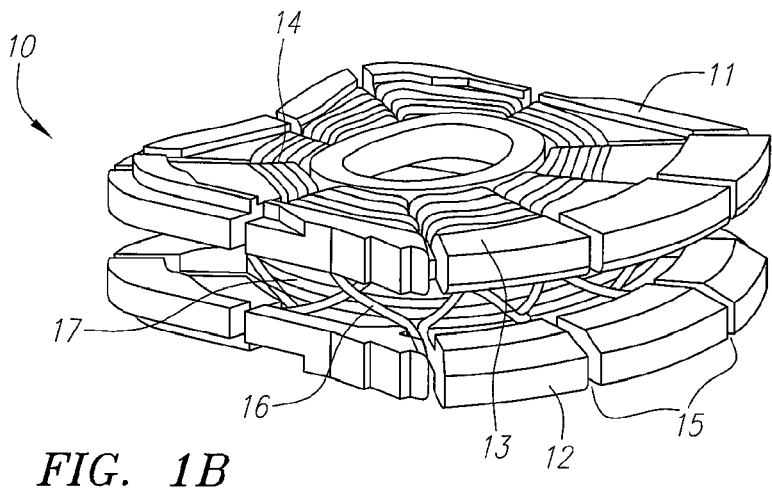

Two different representative intervertebral discs are shown in FIGS. 1A and 1B. As can be seen in FIGS. 1A and 1B, prosthetic discs 10 each include a top endplate 11 and a lower endplate 12. Top and bottom endplates 11 and 12 are planar substrates, where these plates typically have a length from about 12 mm to about 45 mm, such as from about 13 mm to about 44 mm, a width of from about 11 mm to about 28 mm, such as from about 12 mm to about 25 mm and a thickness of from about 0.5 mm to about 4 mm, such as from about 1 mm to about 3 mm. The top and bottom endplates are fabricated from a physiologically acceptable material that provides for the requisite mechanical properties, where representative materials from which the endplates may be fabricated are known to those of skill in the art and include, but are not limited to: titanium, titanium alloys, stainless steel, cobalt/chromium, etc.; plastics such as polyethylene with ultra high molar mass (molecular weight) (UHMW-PE), polyether ether ketone (PEEK), etc.; ceramics; graphite; etc. As shown in FIGS. 1A and 1B, separating the top and bottom endplates is a fibrous compressible element 17. The thickness of the fibrous compressible element may vary, but ranges in many embodiments from about 2 mm to about 10 mm, including from about 3 mm to about 8 mm.

The disc is further characterized in that it includes an annular region 13 (i.e., annulus), which is the region, domain or area that extends around the periphery of the disc, and a nuclear region (i.e., nucleus) 14, which is the region, domain or area in the center of the disc and surrounded by the annulus.

While in the broadest sense the plates may include a single region around which a fiber is wound in order to hold the plates together, in many embodiments the plates have a plurality of such regions. As shown in FIGS. 1A and 1B, endplates 11 and 12 include a plurality of slots 15 through which fibers, e.g., of the fibrous compressible element, may be passed through or wound, as shown. In many embodiments, the number of different slots present in the periphery of the device ranges from about 4 to about 36, such as from about 5 to about 25. As shown in FIGS. 1A and 1B, at least one fiber 16 of the fibrous compressible element is wrapped around a region of the top and bottom plates, e.g., by being passed through slots in the top and bottom plates, in order to hold the plates together.

The fibrous compressible elements, 17, are typically made up of one or more fibers, where the fibers are generally high tenacity fibers with a high modulus of elasticity. By high tenacity fibers is meant fibers that can withstand a longitudinal stress without tearing asunder of at least about 50 MPa, such as at least about 250 MPa. As the fibers have a high modulus of elasticity, their modulus of elasticity is typically at least about 100 MPa, usually at least about 500 MPa. The fibers are generally elongate fibers having a diameter that ranges from about 3 µm to about 8 µm, such as about 4 µm to about 7 µm, where the length of each individual fiber making up the fibrous component may range from about 1 m to about 20 m, such as from about 2 m to about 15 m.

The fibers making up the fibrous compressible may be fabricated from any suitable material, where representative materials of interest include, but are not limited to: polyester (e.g., Dacron), polyethylene, polyaramid, carbon or glass fibers, polyethylene terephthalate, arcrylic polymers, methacrylic polymers, polyurethane, polyurea, polyolefin, halogenated polyolefin, polysaccharide, vinylic polymer, polyphosphazene, polysiloxane, and the like.

The fibrous compressible made up of one or more fibers wound around one or more regions of the top or bottom plates may make up a variety of different configurations. For example, the fibers may be wound in a pattern that has an oblique orientation to simulate the annulus of intact disc, where a representative oblique fiber configuration or orientation is shown in FIG. 1A. The number of layers of fiber winding may be varied to achieve similar mechanical properties to an intact disk. Where desired, compliancy of the structure may be reduced by including a horizontal winding configuration, as shown in FIG. 1B.

Figure 2:
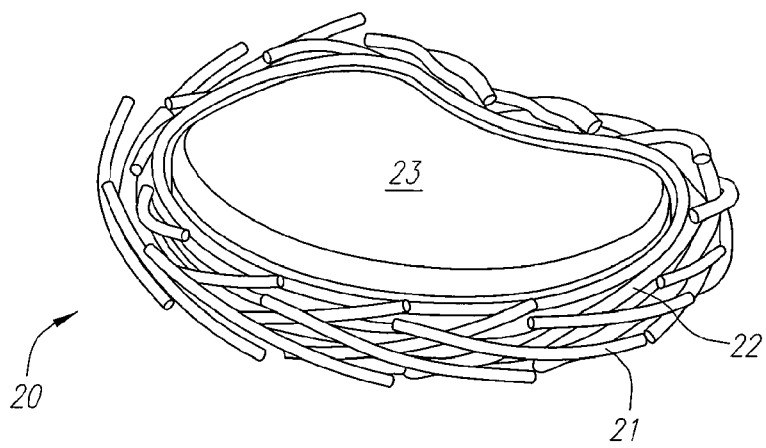
FIG. 2 provides a three-dimensional view of a fibrous compressible element that includes a polymeric nucleus and a fibrous annulus according to one embodiment of the subject invention.

In certain embodiments, the fibrous compressible element 20 has a fibrous component 21 limited to the annular region of the disc 22, e.g., to the region along the periphery of the disc. FIG. 2 provides a representation of this embodiment, where the fibrous component is limited solely to the annular region of the disc and includes both oblique and horizontal windings. Also shown is a separate polymeric component 23 present in the nucleus.

Figure 3A:
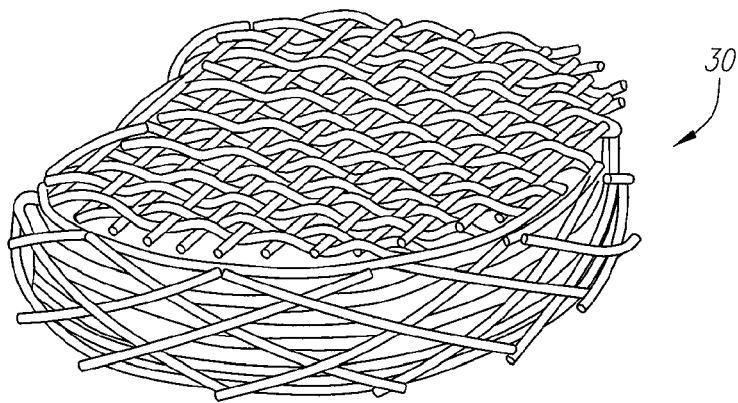
FIGS. 3A to 3C provide different views of a fibrous component of the fibrous compressible elements according to an embodiment of the subject invention.
Figure 3B:
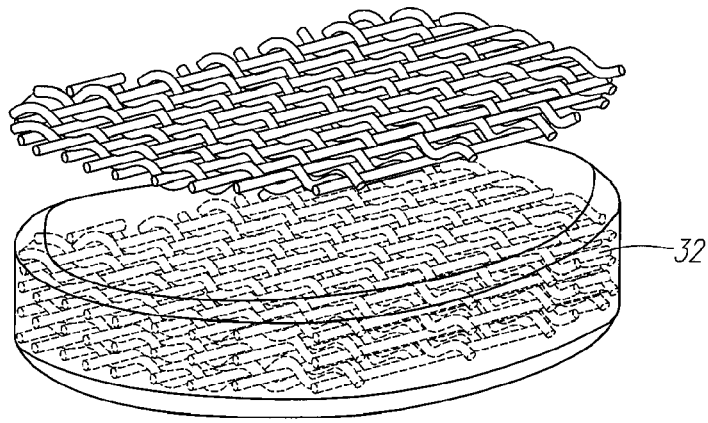
Figure 3C:
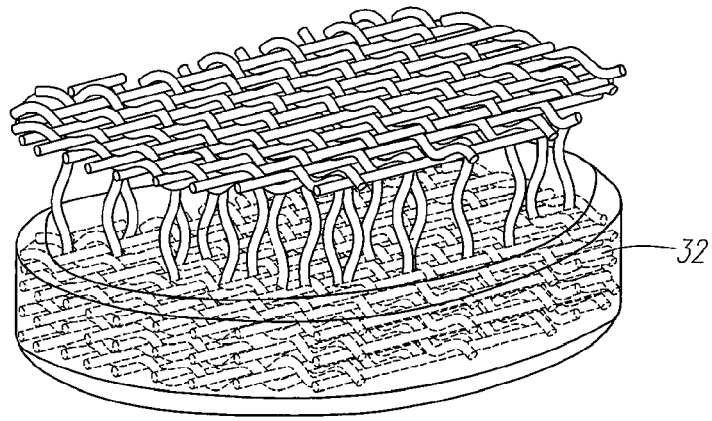

In yet other embodiments the fibrous component of the fibrous compressible element may extend beyond the annular region of the disc into at least about a portion, if not all, of the nucleus. FIG. 3A provides a view of a fibrous component 30 that occupies both the annular and nuclear regions of the disc, where the annular region of the disc is made up of fiber windings that are both oblique and horizontal, as described above, while the nucleus of the disc is occupied by fibers woven into a three-dimensional network that occupies the nuclear space. Instead of a three-dimensional network structure, one may have multiple two dimensional layers of interwoven fibers stacked on top of each other, as shown in FIG. 3B, where the multiple stacked layers may be stitched to each other, as shown in FIG. 3C. By adjusting one or more parameters of the fibrous component, such as the density of the fibers, number of layers, frequency of stitching, and the like, the mechanical properties of the fibrous component can be tailored as desired, e.g., to mimic the mechanical properties of a natural intervertebral disc. Also shown in FIGS. 3B and 3C is the outline of a polymeric component 32 in which the fibrous component 30 is embedded.

In certain embodiments, the fibrous compressible element further includes one or more polymeric components. The polymeric component(s), when present, may be fabricated from a variety of different physiologically acceptable materials. Representative materials of interest include, but are not limited to: elastomeric materials, such as polysiloxane, polyurethane, poly(ethylene propylene) copolymer, polyvinylchloride, poly(tetrafluoro ethylene) and copolymers, hydrogels, and the like.

The polymeric component may be limited to particular domains, e.g., the annular and/or nucleus domains, or extend throughout the entire region of the fibrous compressible elements positioned between the two endplates. As such, in certain embodiments the polymeric component is one that is limited to the nuclear region of the disc, as shown in FIG. 2. In FIG. 2, fibrous compressible element 20 includes a distinct fibrous component 21 that is located in the annular region of the disc 22, while polymeric component 23 is located in the nuclear region of the disc. In other embodiments, the polymeric component is located in both the annular and nuclear regions. In yet other embodiments, the polymeric component may be located solely in the annular region.

Depending on the desired configuration and mechanical properties, the polymeric component may be integrated with the fibrous component, such that at least a portion of the fibers of the fibrous component is embedded in, e.g., complexed with, at least a portion of the polymeric component. In other words, at least a portion of the fibrous component is impregnated with at least a portion of the polymeric component. For example, as shown in FIG. 3B, stacked two-dimensional layers of the fibrous component 30 are present inside the polymeric component 32, such that the fibrous component is impregnated with the polymeric component.

In those configurations where the fibrous and polymeric components are present in a combined format, e.g., as shown in FIG. 3B, the fibers of the fibrous component may be treated to provide for improved bonding with the polymeric component. Representative fiber treatments of interest include, but are not limited to: corona discharge, $O_2$ plasma treatment, oxidation by strong acid ($HNO_3$, $H_2SO_4$). In addition, surface coupling agents may be employed, and/or a monomer mixture of the polymer may be polymerized in presence of the surface-modified fiber to produce the composite fiber/polymeric structure.

As indicated above, the devices may include one or more different polymeric components. In those embodiments where two or more different polymeric components are present, any two given polymeric components are considered different if they differ from each other in terms of at least one aspect, e.g., composition, cross-linking density, and the like. As such, the two or more different polymeric components may be fabricated from the same polymeric molecules, but differ from each other in terms of one or more of: cross-linking density; fillers; etc. For example, the same polymeric material may be present in both the annulus and nucleus of the disc, but the crosslink density of the annulus polymeric component may be higher than that of the nuclear region. In yet other embodiments, polymeric materials that differ from each other with respect to the polymeric molecules from which they are made may be employed.

By selecting particular fibrous component and polymeric component materials and configurations, e.g., from the different representative formats described above, a disc with desired functional characteristics, e.g., that mimics the functional characteristics of the naturally occurring disc, may be produced.

Representative particular combinations of interest include, but are not limited to, the following:
1. Biocompatible polyurethane, such as Ethicon Biomer, reinforced with Dacron poly(ethylene terephthalate) fiber, or Spectra polyethylene fiber, or Kevlar polyaramide fiber, or carbon fiber.
2. Biocompatible polysiloxane modified styrene-ethylene butylene block copolymer sold under C-Flex tradename reinforced with Dacron poly(ethylene terephthalate) fiber, or Spectra polyethylene fiber, or Kevlar polyaramide fiber, or carbon fiber.
3. Biocompatible Silastic silicone rubber, reinforced with Dacron poly(ethylene terephthalate) fiber, or Spectra polyethylene fiber, or Kevlar polyaramide fiber, or carbon fiber.

In using the subject discs, the prosthetic disc is fixed to the vertebral bodies between which it is placed. More specifically, the upper and lower plates of the subject discs are fixed to the vertebral body to which they are adjacent. As such, the subject discs are employed with vertebral body fixation elements during use. In certain embodiments, the vertebral body fixation elements are integral to the disc structure, while in other embodiments the vertebral body fixation elements are separate from the disc structure.

Figure 4A:
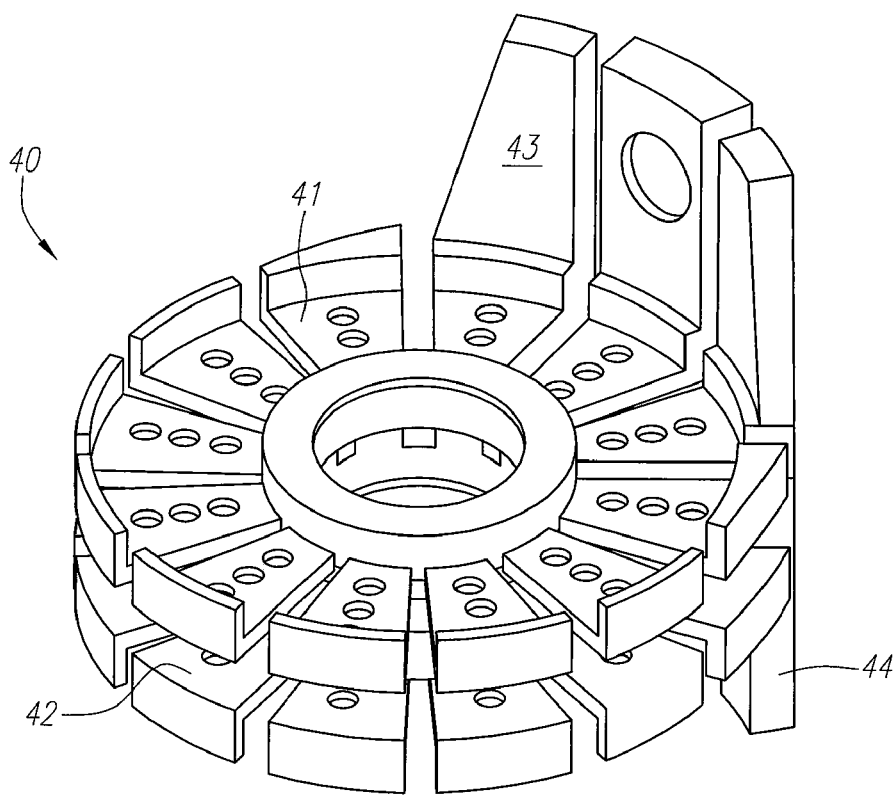
Figure 4B:
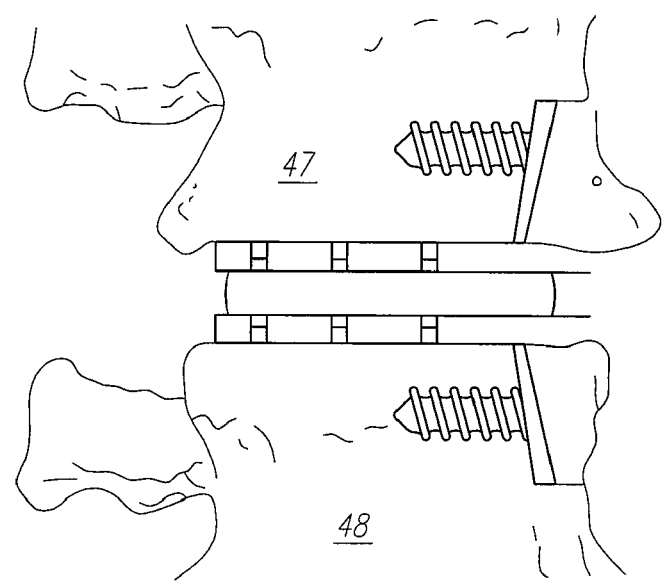
FIG. 4B shows the disc of FIG. 4A implanted with the use of bone screws.

A representative embodiment of those devices where the vertebral body fixation elements are integral with the disc structure is depicted in FIGS. 4A and 4B. FIG. 4A shows device 40 made up of top and bottom endplates 41 and 42. Integrated with top and bottom endplates 41 and 42 are vertebral body fixation elements 43 and 44. The vertebral body fixation elements include holes through which bone screws may be passed for fixation of the disc to upper and lower vetrebral bodies 47 and 48 upon implantation, as represented in FIG. 4B.

Figure 7:
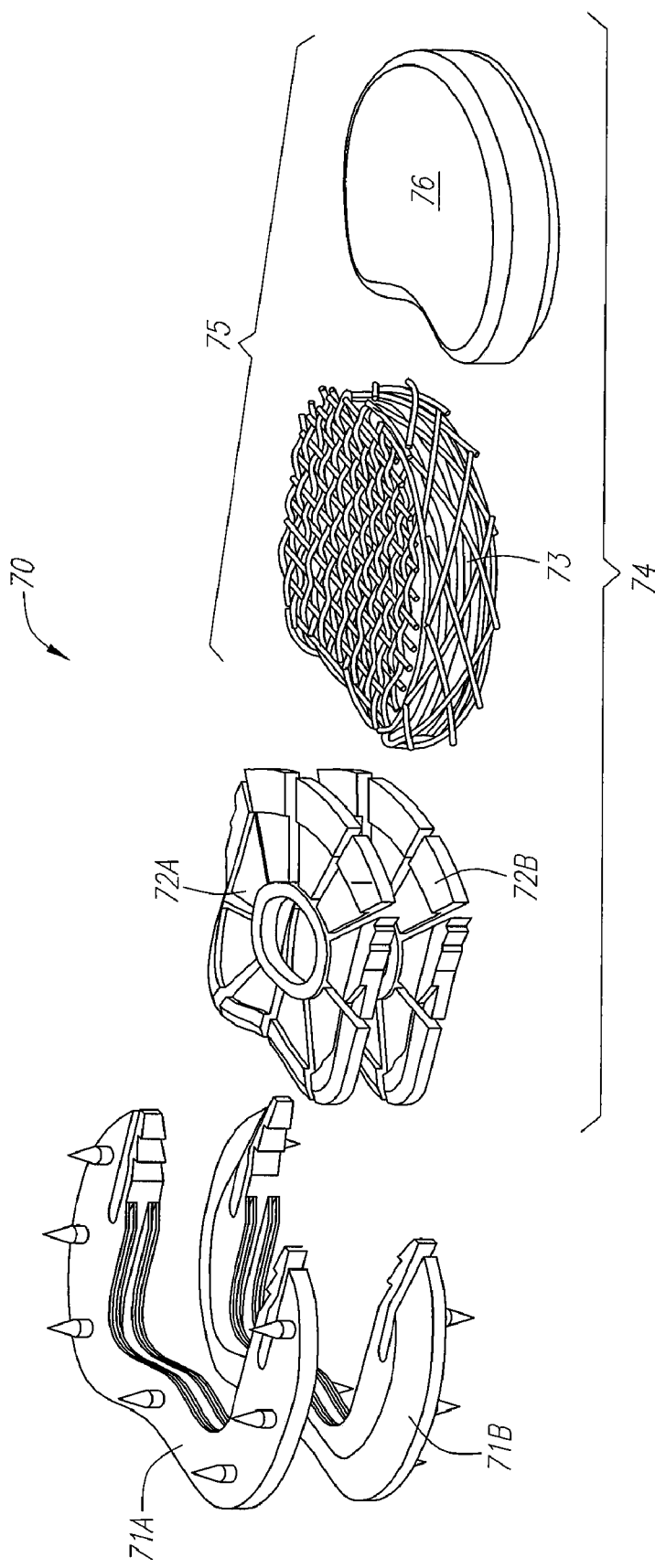
FIG. 7 provides an exploded view of a disc system that includes both an intervertebral disc and vertebral body fixation elements, according to an embodiment of the present invention.

In an alternative embodiment, the disc does not include integrated vertebral body fixation elements, but is designed to mate with separate vertebral body fixation elements, e.g., as depicted in FIG. 7. In other words, the disc is structured to interface with separate vertebral body fixation elements during use. Any convenient separate vertebral body fixation element may be employed in such embodiments, so long as it stably positions the prosthetic disc between two adjacent vertebral bodies.

Figure 5A:
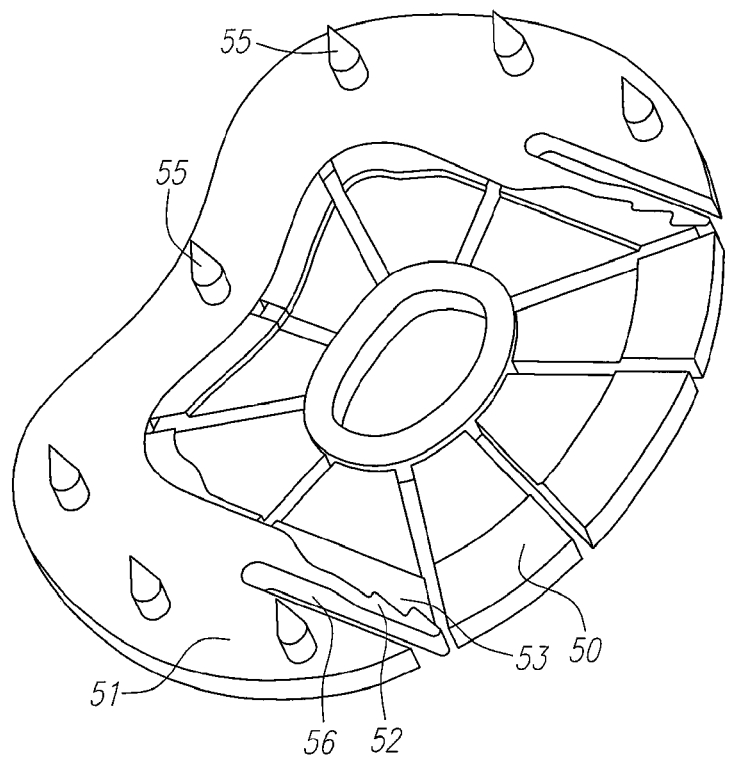
FIGS. 5A to 5C show the mating interface between disc top endplate with an upper vertebral body fixation element according to an embodiment of the subject invention.
Figure 5B:
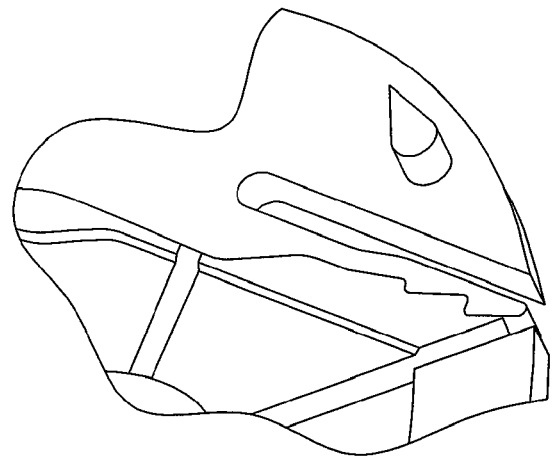
Figure 5C:
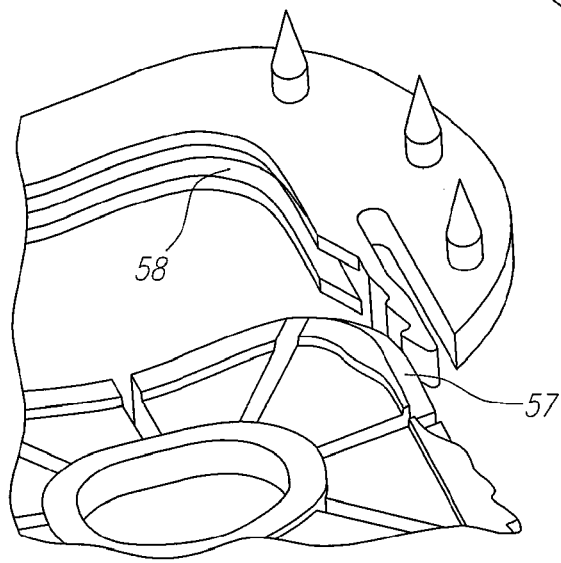

One representative non-integrated vertebral body fixation element according to this embodiment is shown in FIGS. 5A to 5C. FIG. 5A provides a representation of the upper plate 50 of a prosthetic disc mated with a vertebral body fixation element 51, as the structures would appear upon implantation. Vertebral body fixation element 51 is a horseshoe shaped structure having spikes 55 at locations corresponding to the cortical bone of vertebrae and porous coating to enhance bone fixation. The fixation element 51 also has gear teeth 52 such that corresponding gear teeth 53 of the disc upperplate 50 can slide through the gear contact resulting in the right location of prosthetic disc with respect to the fixation element. The gear teeth have a shape such that only inward movement of the upper plate upon implantation is possible. Also present are slots 56 in the spiked fixation elements next to the gear teeth that provide for the elastic deformation of the whole teeth area upon implantation and desirable clearance between mating gear teeth of the disc and fixation element so that incoming gear teeth of the disc can easily slide into the fixation element.

In the embodiment shown in FIG. 5A, as the disc is pushed into the fixation element, the protruded rail 57 on the disc slides along the corresponding concave rail-way 58 on the fixation element until the protruded rail on the most front side is pushed into the corresponding concave rail-way on the fixation element, as shown in FIG. 5C. This rail interface is devised to prevent the upward/downward movement of the top disc endplate and the bottom disc endplate with respect to the corresponding fixation element. This interface between the fixation elements and the top and bottom endplates of the disc enables an easy surgical operation. Specifically, the fixation elements are transferred together to the disc replacement area (disc void space) with an instrument and pushed in the opposite directions toward the vertebrae until they are fixed to the vertebrae, and then the prosthetic disc is transferred by the instrument between the fixation elements and simply pushed inward until the stoppers mate the corresponding stoppers. The prosthetic disc can also be easily removed after long-term use. For its removal, the gear teeth on the fixation element are pushed to reduce the gap of the slot so that the gear engagement between the disc endplate and the fixation element is released.

Figure 6A:
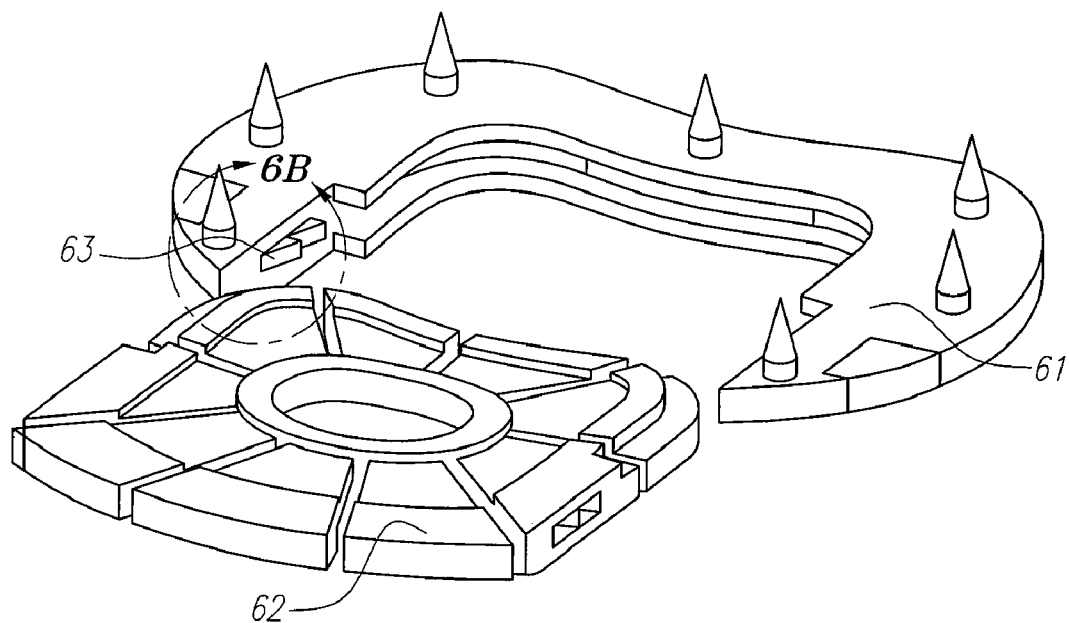
FIGS. 6A and 6B show the mating interface between disc top endplate with an upper vertebral body fixation element according to an alternative embodiment of the subject invention. The top endplate is clamped by a clamping element connected to the upper vertebral body fixation element through a spring.
Figure 6B:
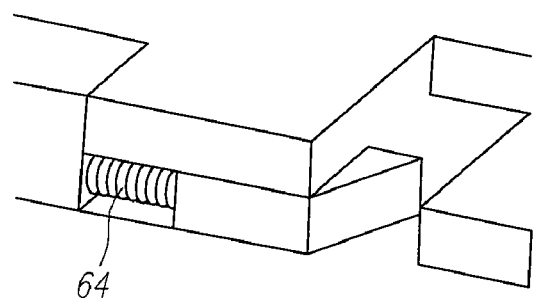

An alternative embodiment is depicted in FIGS. 6A and 6B. In the embodiment shown in FIGS. 6A and 6B, the fixation element 61 and the endplate 62 have a different mating interface from that depicted in FIG. 5A to FIG. 5C. As shown in FIGS. 6A and 6B, the gear teeth in the endplate are brought in contact with the corresponding gear teeth of the clamping element 63 that is attached to the fixation element 61 through a spring 64. In this mechanism, the slots next to the gear teeth shown in the embodiment depicted in FIG. 5A to FIG. 5C are replaced by a spring attached to the the fixation element and this spring deformation provides the necessary recess of the clamping element as the disc endplate is pushed in upon implantation. The gear teeth contact between the endplate and the clamping element allows one way sliding. The disc endplates and the fixation elements have the rail interface as in FIG. 5A to FIG. 5C to prevent the vertical movement.

Systems

Also provided are systems that include at least one component of the subject prosthetic discs, as described above. The systems of the subject invention typically include all of the elements that may be necessary and/or desired in order to replace an intervertebral disc with a prosthetic disc as described above. As such, at a minimum the subject systems include a prosthetic disc according to the present invention, as described above. In addition, the systems in certain embodiments include a vertebral body fixation element, or components thereof, e.g., the fixation elements shown in FIGS. 5A to 6B, bone screws for securing integrated fixation elements as shown in FIGS. 4A and 4B, and the like. The subject systems may also include special delivery devices, e.g., as described in greater detail below.

One specific representative system of particular interest is depicted in FIG. 7. The system 70 of FIG. 7 is depicted as an exploded view, and includes upper and lower fixation elements 71A and 71B, and disc 74 made up of top and bottom endplates 72A and 72B, as well as the fibrous compressible element 75, made up of both a fibrous component 73 and polymeric component 76 of the prosthetic disc.

Methods of Use

Also provided are methods of using the subject prosthetic intervertebral discs and systems thereof. The subject prosthetic intervertebral discs and systems thereof find use in the replacement of damaged or dysfunctional interverterbral discs in vertebrate organisms. Generally the vertebrate organisms are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In many embodiments, the subjects will be humans.

In general, the devices are employed by first removing the to be replaced disc from the subject or patient according to standard protocols to produce a disc void space. Next, the subject prosthetic disc is implanted or positioned in the disc void space, resulting in replacement of the removed disc with the prosthetic disc. This implantation step may include a vertebral body fixation element implantation substep, a post implantation vertebral body securing step, or other variations, depending on the particular configuration of the prosthetic device being employed. In addition, the implantation step described above may include use of one or more implantation devices (or disc delivery devices) for implanting the system components to the site of implantation.

A representative implantation protocol for implanting the device depicted in FIG. 7 is now provided. First, the spine of a subject is exposed via a retroperitoneal approach after sterile preparation. The intervertebral disc in trauma condition is removed, and the cartilage endplates above and below the disc are also removed to the bony end plates to obtain the bleeding surface for the bone growth into porous cavities in the spiked fixation elements 71A and 72A. The gap resulting from these removals is measured and the proper artificial disk assembly is chosen according to the measurement.

The spiked fixation element plates are loaded onto a delivery instrument 80 as shown in FIGS. 8 and 9 such that relative location and orientation between the upper spiked fixation element plate and the lower spiked fixation element plate are kept at a desired configuration. This configuration can be realized by providing appropriate mating features on the instrument and the corresponding mating features on the spiked plates. One of the possible mating features would be the pocket of the instrument and the corresponding external faces of the spiked plates as shown in FIG. 8. The pocket has the same internal face as the external face of spiked plates but with a slightly smaller size such that the spiked plate fits tightly into the pocket of the instrument. The instrument together with the spiked fixation plates is delivered to the area where the disc was removed and the spiked plates are pushed against the vertebra using the distracting motion of the instrument as shown in FIG. 9.

Figure 10:
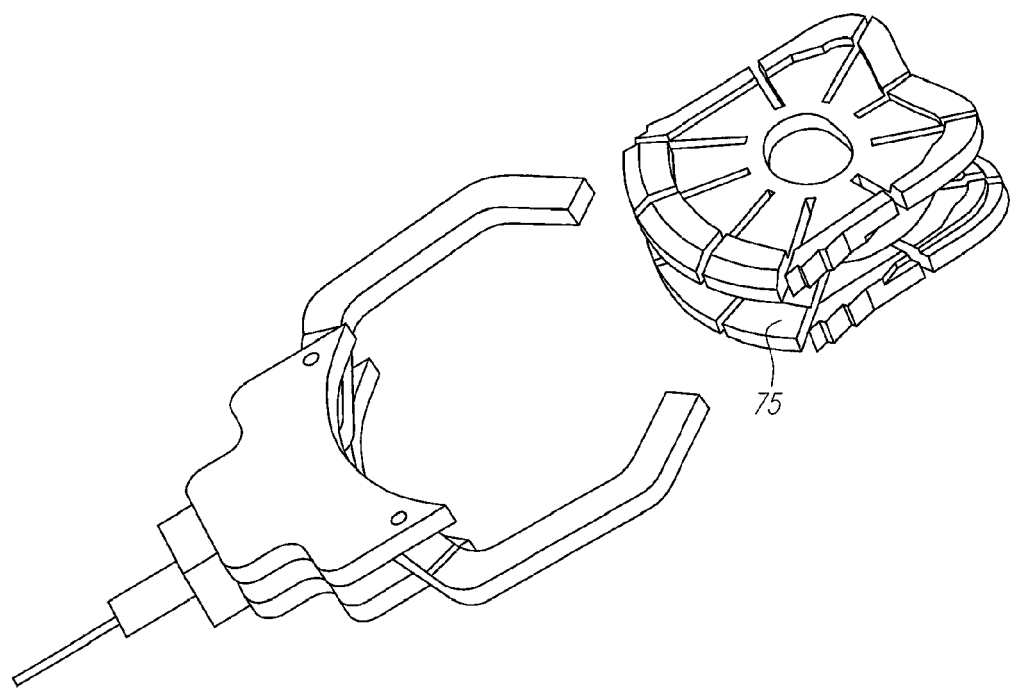
FIG. 10 provides a view of disc implantation device and disc according to an embodiment of the subject invention.

Once the spiked fixation plates are firmly fixed to the vertebra, the prosthetic disc 75 is held by a different tool and inserted into the implanted spiked fixation plates such that its gear teeth go through the matching gear teeth on the spiked fixation plates. FIG. 10 shows the tool holding the disc. The grippers in FIG. 10 hold the fiber area of the disc when it is in grasp position. The disc accommodating the grippers has the circular concave area in contact with the disc and is pushed into the spiked fixation plates through this contact. When the disc is inserted all the way into the spiked plates, the protruded rails on the disc at its most front side are in contact with the female railway of the spiked fixation plates and the disc is secured between the spiked fixation plates and therefore the vertebra.

Figure 11:
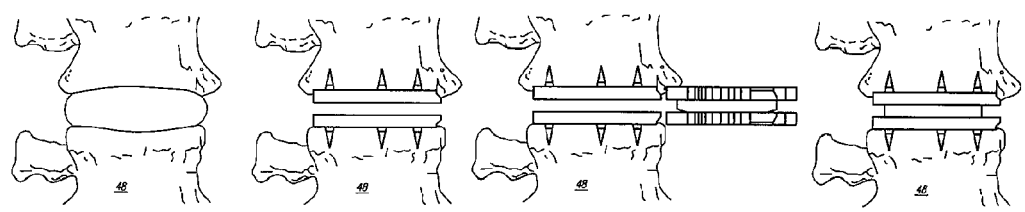
FIG. 11 provides sequential views of a disc being replaced with a prosthetic disc according to a method of the subject invention.

The above-described protocol is depicted in FIG. 11.

The above specifically reviewed protocol is merely representative of the protocols that may be employed for implanting devices according to the subject invention.

Kits

Also provided are kits for use in practicing the subject methods, where the kits typically include one or more of the above prosthetic intervertebral disc devices (e.g., a plurality of such devices in different sizes), and/or components of the subject systems, e.g., fixation elements or components thereof, delivery devices, etc. as described above. The kit may further include other components, e.g., site preparation components, etc., which may find use in practicing the subject methods.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

It is evident from the above discussion and results that the subject invention provides a significantly improved prosthetic intervertebral disc. Significantly, the subject discs closely imitate the mechanical properties of the fully functional natural discs that they are designed to replace. The subject discs exhibit stiffness in the vertical direction, torsional stiffness, bending stiffness in saggital plane, and bending stiffness in front plane, where the degree of these features can be controlled independently by adjusting the components of the discs, e.g., number of layers of fiber winding, pattern of fiber winding, distribution of impregnated polymer, and the types of impregnated polymers, etc. The fiber reinforced structure of the subject discs prevents the fatigue failure on the inside polymer and the surface treatment on the fiber of certain embodiments eliminates the debris problem, both of which are major disadvantages experienced with certain "rubber-type" artificial disks. The interface mechanism between the fixation plates and the disc plates of certain embodiments of the subject invention, e.g., as shown in FIG. 7, enables a very easy surgical operation.

The surgeon simply needs to push the disc inward after fixing the spiked fixation plates onto the vertebrae. Such embodiments also enable easy removal of the disc in case the surgery brings about an ill effect. The gear teeth on the fixation elements are easily pushed from outside such that the gear engagement between the disc endplates and the fixation elements is released and the disc endplates are pulled out from the spiked plates. In view of the above and other benefits and features provided by the subject invention, it is clear that the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A prosthetic intervertebral disc comprising:
   top and bottom endplates; and
   a fibrous compressible element positioned between said top and bottom endplates, wherein said compressible element has a configuration that includes an annular region and a nuclear region;
   wherein said top and bottom end plates are held together by at least one fiber wound around at least one region of said top end plate and at least one region of said bottom end plate, and wherein said top and bottom endplates each comprise a plurality of peripheral slots through which said at least one fiber passes to attach said top and bottom end plates to said fibrous compressible element.

2. The prosthetic intervertebral disc according to claim 1, wherein said top and bottom endplates comprise mating elements for interfacing with upper and lower vertebral body fixation elements.

3. The prosthetic intervertebral disc according to claim 1, wherein said top and bottom endplates further comprise integrated upper and lower vertebral body fixation elements.

4. The prosthetic intervertebral disc according to claim 1, wherein said fibrous compressible element comprises a fibrous component that is limited to said annular region.

5. The prosthetic intervertebral disc according to claim 1, wherein said fibrous compressible element comprises a fibrous component that extends into at least a portion of said nuclear region.

6. The prosthetic intervertebral disc according to claim 1, wherein said endplates have planar surfaces and wherein said fibrous compressible element comprises a fiber winding pattern that includes at least a component which is oblique with respect to the planar surfaces of the top and bottom plates.

7. The prosthetic intervertebral disc according to claim 6, wherein said fiber winding pattern further includes a component that is horizontal or vertical with respect to the planar surfaces of the top and bottom plates.

8. The prosthetic intervertebral disc according to claim 6, wherein said fibrous compressible element further comprises a three-dimensional woven fabric component.

9. The prosthetic intervertebral disc according to claim 1, wherein said fibrous compressible element is combined with at least one polymeric component.

10. The prosthetic intervertebral disc according to claim 9, wherein said at least one polymeric component is impregnated with fibers of said fibrous compressible element.

11. The prosthetic intervertebral disc according to claim 9, wherein the fibers of said fibrous compressible element are not impregnated with a polymeric component.

12. The prosthetic intervertebral disc according to claim 9, wherein said at least one polymeric component is present in said nucleus region.

13. The prosthetic intervertebral disc according to claim 9, wherein said at least one polymeric component is present in said annular region.

14. The prosthetic intervertebral disc according to claim 9, wherein said disc comprises at least two different polymeric components.

15. A system for replacing an intervertebral disc with a prosthetic intervertebral disc, said system comprising:
   (a) a prosthetic intervertebral disc comprising:
      (i) top and bottom endplates each comprising a plurality of peripheral slots; and
      (ii) a fibrous compressible element positioned between said top and bottom endplates, wherein said compressible element has a configuration that includes an annular region and a nuclear region;
      wherein said top and bottom end plates are held together by at least one fiber wound around at least one region of said top end plate and at least one region of said bottom end plate and passing through at least one of said peripheral slots; and
   (b) upper and lower vertebral body fixation elements that mate respectively with said top and bottom endplates.

16. A method for replacing a intervertebral disc with a prosthetic intervertebral disc, said method comprising:
   (a) implanting into said void disc space created by removing an intervertebral disc a prosthetic intervertebral disc comprising:
      (i) top and bottom endplates each comprising a plurality of peripheral slots; and
      (ii) a fibrous compressible element positioned between said top and bottom endplates, wherein said compressible element has a configuration that includes an annular region and a nuclear region;
      wherein said top and bottom end plates are held together by at least one fiber wound around at least one region of said top end plate and at least one region of said bottom end plate, and passing through at least one of said peripheral slots; and
   (b) attaching said prosthetic intervertebral disc to the vertebra above and below said void disc space.

* * * * *

UNITED STATES PATENT AND TRADEMARK OFFICE
CERTIFICATE OF CORRECTION

PATENT NO. : 7,153,325 B2  Page 1 of 1
APPLICATION NO. : 10/632538
DATED : December 26, 2006
INVENTOR(S) : Daniel H. Kim et al.

It is certified that error appears in the above-identified patent and that said Letters Patent is hereby corrected as shown below:

On the title page, item (73), Assignee: change "Ultra-Kinetics, Inc." to --Spinal Kinetics, Inc.--

Signed and Sealed this

Eighth Day of April, 2008

JON W. DUDAS
*Director of the United States Patent and Trademark Office*